United States Patent
Noetzel et al.

(10) Patent No.: US 7,641,862 B2
(45) Date of Patent: Jan. 5, 2010

(54) ANALYTICAL TEST ELEMENT AND METHOD FOR BLOOD ANALYSES

(75) Inventors: Siegfried Noetzel, Wilhelmsfeld (DE); Jean-Philippe Bogardi, Mannheim (DE); Dieter Mangold, Maxdorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/330,645

(22) Filed: Dec. 9, 2008

(65) Prior Publication Data

US 2009/0087901 A1 Apr. 2, 2009

Related U.S. Application Data

(62) Division of application No. 10/774,247, filed on Feb. 6, 2004, now Pat. No. 7,479,393.

(30) Foreign Application Priority Data

Feb. 7, 2003 (DE) ................. 103 05 050

(51) Int. Cl.
*G01N 1/18* (2006.01)
*G01N 1/10* (2006.01)
*G01N 33/48* (2006.01)
*G01N 33/72* (2006.01)

(52) U.S. Cl. .............. 422/100; 422/99; 422/102; 422/103; 436/63; 436/66; 436/67; 436/180; 436/536; 436/538; 436/539; 435/2; 435/7.1; 435/287.1; 435/287.2; 435/287.3

(58) Field of Classification Search .......... 438/63, 438/66, 67, 174, 175, 177, 178, 179, 180, 438/518, 536, 538–540; 422/68.1, 59, 99, 422/100, 101, 102, 103; 435/2, 7.1, 287.1–287.3
See application file for complete search history.

(56) References Cited

U.S. PATENT DOCUMENTS

| 4,675,117 A | 6/1987 | Neumann et al. |
| 4,970,171 A * | 11/1990 | Messenger et al. ............ 436/66 |
| 5,556,789 A * | 9/1996 | Goerlach-Graw et al. ... 436/169 |
| 6,143,510 A | 11/2000 | Hoshino et al. |
| 6,319,719 B1 | 11/2001 | Bhullar et al. |
| 6,406,672 B1 | 6/2002 | Bhullar et al. |
| 6,475,441 B1 | 11/2002 | Parce et al. |
| 6,521,182 B1 | 2/2003 | Shartle et al. |
| 7,087,203 B2 | 8/2006 | Gordon et al. |
| 7,479,393 B2 * | 1/2009 | Noetzel et al. .............. 436/179 |
| 2003/0003522 A1 | 1/2003 | Goldman |

(Continued)

FOREIGN PATENT DOCUMENTS

DE 43 23 672 A 1/1995

(Continued)

*Primary Examiner*—Maureen M Wallenhorst

(57) ABSTRACT

An analytical test element for blood analyses is provided having an application site and a microfluidic channel structure in fluid communication with the application site. The channel structure includes at least first and second analytical channels for receiving first and second portions of a blood sample applied to the application site. The first analytical channel includes a first analytical site to determine the total haemoglobin value (Hb) of the blood sample. The second analytical channel includes a second analytical site to determine a glycohaemoglobin value (HbA1c) of the blood sample.

14 Claims, 1 Drawing Sheet

U.S. PATENT DOCUMENTS

2005/0136551 A1 * 6/2005 Mpock .................. 436/514

FOREIGN PATENT DOCUMENTS

| EP | A 0989407 B1 | 9/1999 |
| WO | WO 99/18436 A1 | 4/1999 |
| WO | WO0062931 A1 | 10/2000 |
| WO | WO01/24931 A1 | 4/2001 |

* cited by examiner

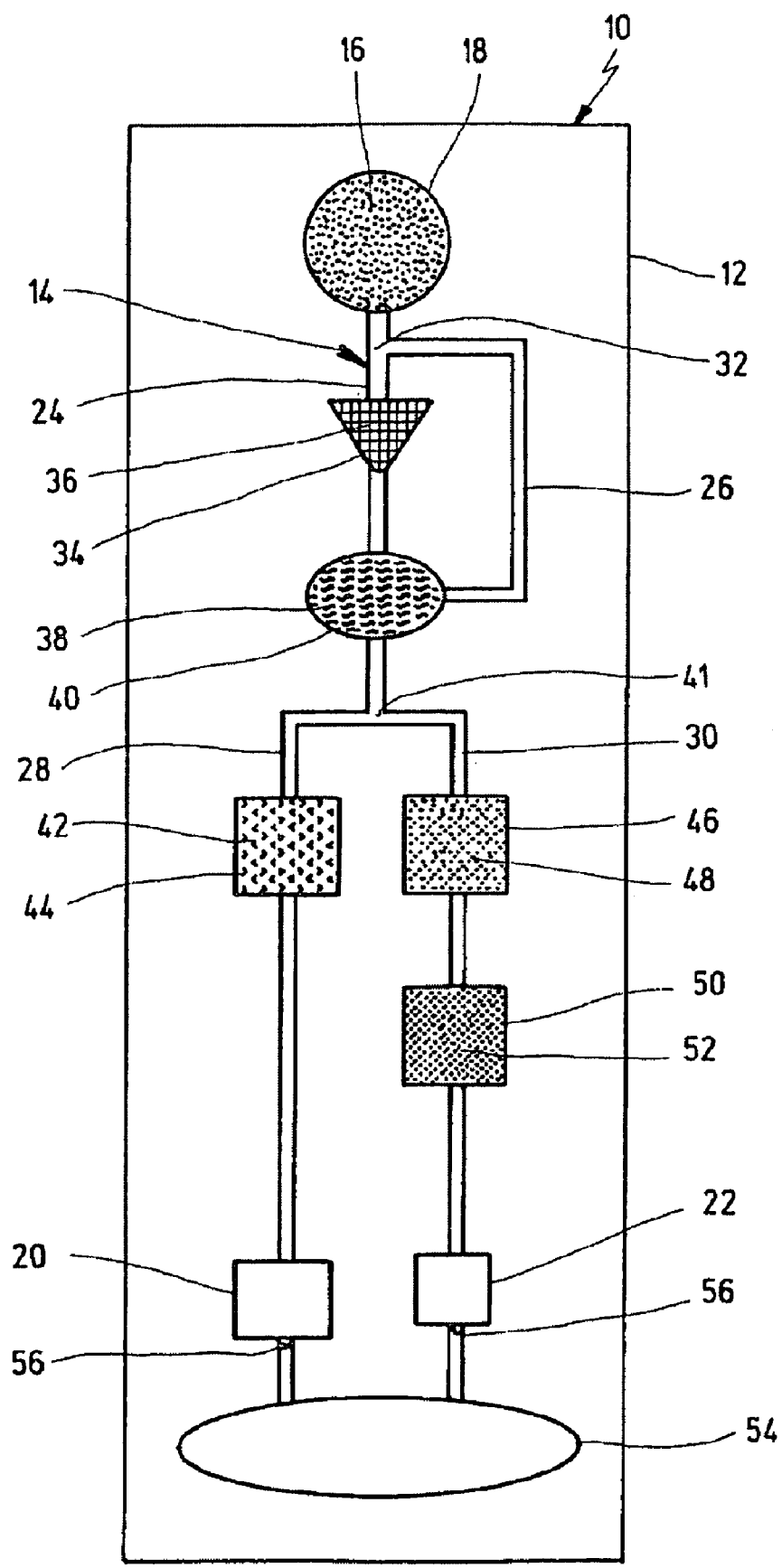

ANALYTICAL TEST ELEMENT AND METHOD FOR BLOOD ANALYSES

CROSS-REFERENCE TO RELATED APPLICATIONS

The application is a division of U.S. Application Ser. No. 10/774,247, filed Feb. 6, 2004 (now U.S. Pat. No. 7,479,393, issued on Jan. 20, 2009), which claims priority under 35 U.S.C. §119 to German Application No. 103 05 050.7 filed Feb. 7, 2003.

BACKGROUND OF THE INVENTION

The invention concerns an analytical test element for blood analyses especially by means of a single-use rapid test comprising a substrate body having a preferably microfluidic channel structure for the flow transport of a blood sample from an application site to at least one analytical site. The invention also concerns a corresponding method for carrying out blood analyses in which a blood sample is conveyed by means of a channel structure in an analytical test element from an application site to at least one analytical site.

A test element of this type is known from WO 01/24931. This application describes a channel or flow structure that is specially designed for separating plasma or serum from a whole blood sample and comprises two capillary-active zones where a first zone is composed of a porous matrix material and a second zone which is in contact with the first zone comprises one or more capillary channels. As a result the plasma obtained in the first zone is made available in the second zone free from interfering components as a target fluid for example for glucose tests.

A test element is generally understood as a carrier-bound fluidic (micro)system for receiving a liquid sample which enables sample preparation for an immediate or later analysis independent of a laboratory environment. Such test elements are usually intended to be single-use articles or disposables for near patient diagnostics in which all reagents that are necessary to carry out the test are provided on the carrier or component so that they can also be used by laymen without requiring special handling.

Such test elements are used as test strips especially for blood glucose monitoring by diabetics. On the other hand, the determination of haemoglobin A1c allows a retrospective estimate of the average glucose concentration over the last weeks and thus of the quality of the metabolic control of the diabetic. HbA1c is defined as haemoglobin A that has been glycated with glucose on the N-terminal valine residues of the β chains. HbA1c is usually stated as a percentage of the total haemoglobin which requires a determination of the haemoglobin concentration from the same blood sample in addition to the HbA1c content. This double determination of Hb and HbA1c has previously been carried out on laboratory instruments that are very complicated to operate and are thus error-prone and expensive.

SUMMARY OF THE INVENTION

It is against the above background that the present invention provides certain unobvious advantages and advancements over the prior art. In particular, the inventors have recognized a need for improvements in analytical test elements and methods for blood analyses.

Although the present invention is not limited to specific advantages or functionality, it is noted that the present invention provides an improved test element such that blood tests can be carried out inexpensively with as little interaction by the user as possible and low consumption of reagents especially when the analyte is present at a high concentration in the initial sample.

In accordance with one embodiment of the present invention, an analytical test element is provided comprising an application site and a microfluidic channel structure in fluid communication with the application site. The channel structure comprises at least first and second analytical channels for receiving first and second portions of a blood sample applied to the application site. The first analytical channel comprises a first analytical site to determine the total haemoglobin value (Hb) of the blood sample. The second analytical channel comprises a second analytical site to determine a glycohaemoglobin value (HbA1c) of the blood sample.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWING

The following detailed description of the embodiments of the present invention can be best understood when read in conjunction with the following drawing, where like structure is indicated with like reference numerals and in which:

FIG. 1 shows an analytical test element in accordance with an embodiment of the present invention for determining Hb and HbA1c values of a blood sample in a rapid test.

Skilled artisans appreciate that elements in the FIGURE are illustrated for simplicity and clarity and have not necessarily been drawn to scale. For example, the dimensions of some of the elements in the FIGURE may be exaggerated relative to other elements to help improve understanding of the embodiment(s) of the present invention.

DETAILED DESCRIPTION OF THE INVENTION

In accordance with one embodiment of the present invention, the channel structure has a dilution channel that can be loaded with a blood sample and contains separation means for retaining corpuscular blood components, and a sample channel for conveying an aliquot of a blood sample to be diluted which is joined to the dilution channel at a mixing site. This enables whole blood that has been applied by the user to be diluted with its own liquid components without having to store additional liquids. The dilution with the sample material is automatically controlled by the flow transport which obviates complicated manual handling steps by the user or complex mechanical interactions by an analyzer.

The blood sample can be advantageously applied to the sample channel and the dilution channel via a junction which also divides the sample flow. In this connection the blood sample can be applied to a central point and be divided at the junction or at a branch of the sample channel in a quantified, predefined ratio such that the sample channel and dilution channel can be loaded with the sample. In order to set a specified ratio for dividing the partial currents of the blood sample that are passed through, it is advantageous when the relative channel cross-sections of the sample and dilution channel are appropriately adapted. In order to reduce the haemoglobin concentration, it is especially advantageous when the rate of flow through the dilution channel is more than 10-times and preferably more than 100-times the rate of flow through the sample channel.

In order to retain cell components it is advantageous when a filter element especially comprising a glass fibre fleece or a microporous filter matrix or filter membrane is located as a separation means in the dilution channel and preferably in a filter chamber. Alternatively or in addition, the dilution channel can have a microstructure geometry designed to retain cell components of the blood sample as the separation means.

Another advantageous embodiment provides that the mixing site comprises a lysis chamber provided with a lysing agent to haemolyse the diluted blood sample.

One aspect and another variant of the invention provides that the channel structure has a first analytical channel for determining the total haemoglobin value (Hb) of the blood sample and a second analytical channel for determining a glycohaemoglobin value (HbA1c) of the blood sample. This enables a HbA1c test to be carried out in allocated flow paths in a one-step test by a simple application of blood to a test element.

An advantageous embodiment provides that the analytical channels are arranged in parallel and can be loaded with the diluted blood sample by means of a branch acting as a current divider downstream of the mixing site.

It is advantageous for the determination of total haemoglobin when the first analytical channel has an oxidation chamber containing an incorporated oxidizing agent and especially ferricyanide to oxidize the released haemoglobin.

The second analytical channel is advantageously designed for the immunoturbidi-metric determination of the glycohaemoglobin concentration. For this purpose the second analytical channel advantageously has a first reaction chamber into which HbA1c antibodies are dispensed and this first reaction chamber is followed by a second reaction chamber containing an agglutinator.

Other basic methods for determining HbA1c in blood are also known to a person skilled in the art for example from EP-A-0 989 407. These methods can also be used in the present invention and are therefore explicitly incorporated.

The end sections of the analytical channels are designed as cuvettes for photometric analysis and thus form analytical sites for a simple, contactless detection.

In order to collect the sample liquid safely and hygienically, it is advantageous when the analytical channels discharge into a collecting reservoir.

An automatic flow transport is achieved by the channel structure having a wholly or partially capillary geometry. It is advantageous for the control of flow transport when the channel structure has wall sections that have for example been modified by surface treatment, plasma treatment or coating. Another advantageous embodiment provides that the channel structure has valve elements to control the flow transport that are in particular in the form of hydrophilic or hydrophobic channel sections. However, it is basically also possible for the flow transport in the channel structure to be controlled externally by external control means acting on the substrate body and in particular by local application of pressure or centrifugal forces.

With regard to the methodology the object mentioned above is achieved by obtaining liquid components from the blood sample that are introduced into a portion of the blood sample to be analysed for the purposes of dilution. An advantageous embodiment provides that a whole blood sample as the starting material is fed into a dilution channel and a sample channel of the channel structure in parallel subflows and that the subflow in the dilution channel which has been depleted of cell components is joined with the subflow in the sample channel at a mixing site.

The invention is elucidated in more detail in the following on the basis of an example of application shown schematically in the drawing. The single FIGURE shows an analytical test element for determining Hb and HbA1c values of a blood sample in a rapid test.

The test element 10 comprises an elongate support or substrate body 12 containing a channel structure 14 formed therein for the flow transport of microscopic sample quantities (µl) of a blood sample 16 to be analysed from an application zone 18 to measuring or analytical sites 20, 22 for Hb and HbA1c.

The substrate body 12 can be formed from plastic as an injection-moulded part or from several layers of foil as a composite part. It is designed to be a consumable or a so-called disposable for a single-use test.

The channel structure 14 can be directly moulded into the substrate body or be formed by special manufacturing steps such as embossing or stamping. At least sections thereof have a suitable capillary geometry for an automatic capillary-active flow transport of the blood fluid.

Starting from the application zone 18 the channel structure 14 has a dilution channel 24, an aliquot or sample channel 26 and two analytical channels 28, 30 leading to the analytical sites 20, 22.

The blood sample 16 can be fed via a junction 32 into the dilution channel 24 and the sample channel 26 whereby the sample flow is split in parallel. Due an appropriate design of the channel cross-sections, the flow rate through the dilution channel 24 is many times higher than the flow rate through the sample channel 26.

The dilution channel 24 contains a separation means 36 in a separation chamber 34 for retaining cell components of the portion of the blood sample 16 that flows through it. Such separation means 36 can for example be in the form of a glass fibre fleece located in the separation chamber 34.

The dilution channel 24 and the sample channel 26 discharge into a mixing or lysing chamber 40 containing a lysing agent 38. The outlet side communicates via a branch 41 as a flow divider with the analytical channels 28, 30.

An oxidation chamber 44 containing an oxidizing reagent 42 such as potassium hexacyanoferrate is located in the first analytical channel 28 for oxidizing released haemoglobin. The analytical site 20 located downstream thereof is designed as a cuvette for a photometric determination of Hb.

The second analytical channel 30 is used for the immunoturbidimetric determination of glycated haemoglobins. For this purpose it has a first reaction chamber 46 containing HbA1c antibodies 48 dispensed therein and a subsequent second reaction chamber 50 containing an agglutination agent 52 for excess HbA1c antibodies. The second analytical site 22 is located downstream thereof and is also designed as a cuvette for a photometric measurement of turbidity.

Both analytical channels 20, 22 discharge into a common collecting reservoir 54 as waste for the examined liquid samples. Barriers or valve elements 56 comprising hydrophilic or hydrophobic surface modifications may be located on the outlet side of the cuvettes 20, 22 and optionally of the chambers 40, 44, 46, 50 to control the flow transport. These elements allow a control of reaction processes and in particular the control of the sample volume and measuring process, the dissolution of incorporated dry reagents and their mixing in the reaction chambers e.g., by temporarily interrupting the liquid flow.

In order to carry out an in vitro rapid test for determining glycated haemoglobin, a small amount of whole blood is applied by a user to the application zone 18. An aliquot thereof is conveyed via the sample channel 26 into the lysing chamber 40 and is mixed there with the plasma obtained by removing erythrocytes in the dilution channel 24. This results in a defined dilution or reduction of the analyte concentration without having to process additional dilution liquids. At the same time the sample is mixed in the lysing chamber 38 with the lysing agent 38 (for example saponin) provided as a dry substance which lyses the erythrocytes and releases the red-pigmented haemoglobin.

A portion of the diluted haemolysate is conveyed via the branch 41 into the first analytical channel 28 and is converted in the oxidation chamber 44 into a derivative having a characteristic spectrum. After it has passed into the cuvette 20, the total haemoglobin concentration Hb can be measured by a photometer that is not shown.

For the glycohaemoglobin determination another portion of the diluted haemolysate is passed via the branch 41 into the second analytical channel 30. In the first reaction chamber of this channel the glycohaemoglobin HbA1c from the sample is mixed with an excess of HbA1c antibodies 48 and converted into a soluble antigen-antibody complex. The remaining free antibodies 48 are agglutinated in the second reaction chamber 50 and subsequently measured turbidimetrically in the cuvette 22. The change in turbidity is inversely proportional to the amount of bound glyco-haemoglobin. The final result is subsequently calculated as a ratio of HbA1c to Hb.

The test procedure described above enables a one-step procedure without having to store or add additional liquids. It is obvious that the controlled dissolution of dispensed and dried reagents in automatically regulated microfluidic reaction paths also enables other embodiments of a HbA1c test which also include the use of other methods of determination in which the plasma volume obtained can also be used in subsequent process steps e.g., to wash out excess reagents. It is basically possible for the Hb and HbA1c determination to be carried out in channel sections arranged in series and optionally also without prior sample dilution. It is also conceivable that at least a part of the channel structure is formed by a porous matrix material.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An analytical test element comprising:
   an application site, and
   a microfluidic channel structure in fluid communication with said application site, said channel structure comprising at least first and second analytical channels for receiving first and second portions of a blood sample applied to the application site, wherein
   said first analytical channel comprises a first analytical site to determine the total haemoglobin value (Hb) of the blood sample, and
   said second analytical channel comprises a second analytical site to determine a glycohaemoglobin value (HbA1c) of the blood sample.

2. The analytical test element of claim 1, wherein the first analytical channel further comprises an oxidation chamber positioned upstream of said first analytical site and containing a stored oxidizing agent to oxidize released haemoglobin.

3. The analytical test element of claim 2, wherein the stored oxidizing agent is ferricyanide.

4. The analytical test element of claim 1, wherein the second analytical channel is designed for the immuno-turbidimetric determination of the glycohaemoglobin value.

5. The analytical test element of claim 1, wherein the second analytical channel has a first reaction chamber positioned upstream of said second analytical site and containing HbA1c antibodies dispensed therein to form soluble antigen-antibody complexes with the glycohaemoglobin from the blood sample.

6. The analytical test element of claim 5, wherein the second analytical channel has a second reaction chamber positioned downstream of the first reaction chamber and upstream of said second analytical site in which an agglutinator is stored to form insoluble immunocomplexes with excess HbA1c antibodies.

7. The analytical test element of claim 1, wherein the first and second analytical sites are each configured as a cuvette for a photometric measurement.

8. The analytical test element of claim 1, wherein the first and second analytical channels discharge into a collecting reservoir.

9. The analytical test element of claim 1, wherein the channel structure at least in a section thereof has a capillary geometry for an automatic capillary-active flow transport.

10. The analytical test element of claim 9, wherein the channel structure has wall structures for regulating the flow transport.

11. The analytical test element of claim 10, wherein the wall structures are modified by surface treatment, plasma treatment or coating.

12. The analytical test element of claim 9, wherein the channel structure has one or more valve elements for regulating the flow transport.

13. The analytical test element of claim 12, wherein the valve elements are formed by hydrophilic or hydrophobic channel sections.

14. The analytical test element of claim 9, wherein the flow transport in the channel structure is regulated by local application of pressure or centrifugal forces.

* * * * *